Figure 1:
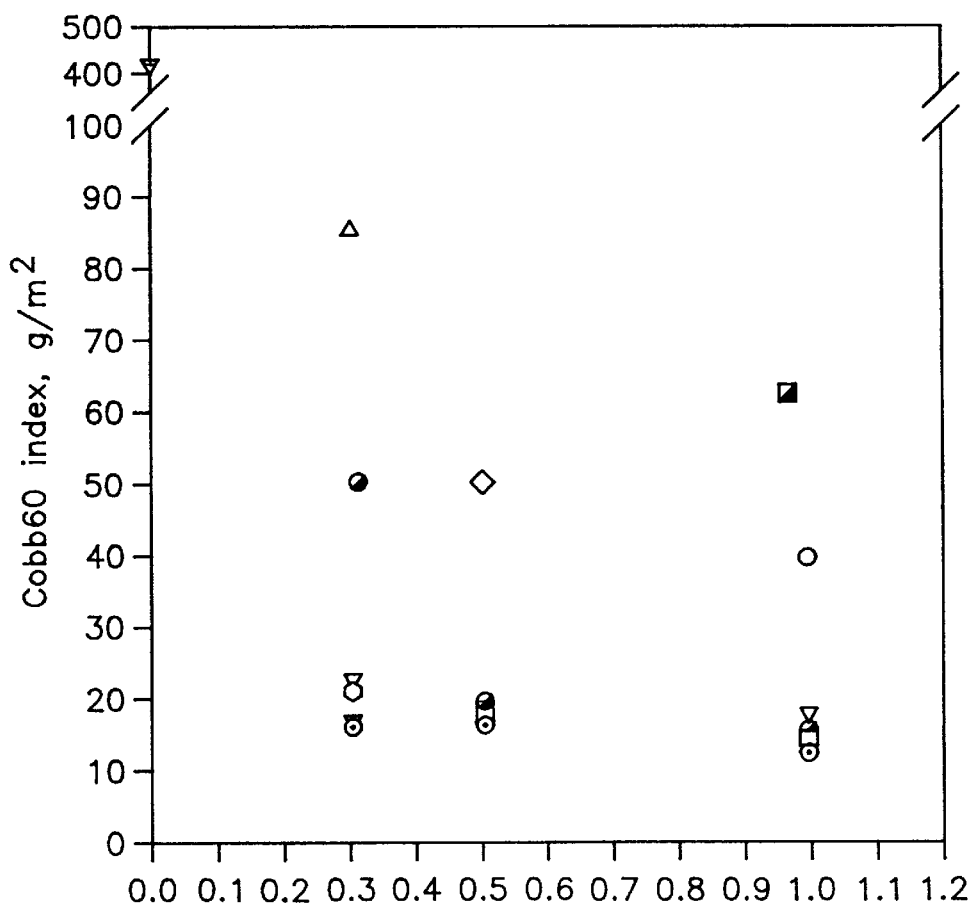

United States Patent [19]

Kapanen et al.

[11] Patent Number: 5,939,562
[45] Date of Patent: Aug. 17, 1999

[54] ALKENYL SUBSTITUTED CYCLIC CARBOXYL ACID ANHYDRIDES AND THEIR APPLICATION IN HYDROPHOBIC PAPER SIZING

[75] Inventors: Mika Kapanen, Porvoo; Salme Koskimies, Helsinski; Jaana Rantanen, Helsinski; Erkki Halme, Helsinski; Raija Savolainen, Raija, all of Finland

[73] Assignee: NESTE OY, Espoo, Finland

[21] Appl. No.: 08/809,893

[22] PCT Filed: Oct. 4, 1995

[86] PCT No.: PCT/FI95/00541

§ 371 Date: Jun. 19, 1997

§ 102(e) Date: Jun. 19, 1997

[87] PCT Pub. No.: WO96/11193

PCT Pub. Date: Apr. 18, 1996

[30] Foreign Application Priority Data

Oct. 7, 1994 [FI] Finland ................................ 944690

[51] Int. Cl.[6] .................................................. C07D 307/36
[52] U.S. Cl. ........................ 549/255; 162/168.1; 162/169
[58] Field of Search ..................... 507/221, 118; 162/168.1, 169; 549/255

[56] References Cited

U.S. PATENT DOCUMENTS 4,576,680 3/1986 Kawatani ................... 162/158
4,736,044 4/1988 Hanson ..................... 549/255

FOREIGN PATENT DOCUMENTS 0169250 1/1986 European Pat. Off. .
0522564 1/1993 European Pat. Off. .
2126260 3/1984 United Kingdom .

OTHER PUBLICATIONS

CA:66:77993, abs of "Extraction and chromatographic equilibria of oils" Reveda, Ropa Uhlie, 8(11)pp. 323–327 1996.

CA:114:210289, abs of "Synthetic petroleum products bsed on n–butylene oligomers". Zeinalov, Azerb. Neft. Khoz., (2) pp. 51–52, 1990.

CA:105:228822, abs of JP6116049 Jul. 1986.

WPIDS accession no 74–71819V Jul. 1974.

Primary Examiner—Gary Geist
Assistant Examiner—Jean F Vollano
Attorney, Agent, or Firm—Birch, Stewart,, Kolasch & Birch, LLP

[57] ABSTRACT

The invention relates to alkene-substituted cyclic carboxylic acid anhydrides which are formed from the reaction of a cyclic carboxylic acid anhydride, including succinic anhydride, and an olefin blend. The olefin blend is made up of internal linear and branched olefins and linear and/or branched α-olefins, in which blend the olefins contain 13–25 carbon atoms. The alkene-substituted cyclic carboxylic acid anhydride can be used for the preparation of an ASA sizing agent suitable for paper sizing.

26 Claims, 1 Drawing Sheet

COBB60 indices of ASA's according to the examples, at different ASA concentrations ASA concentration, wt. %, calculated from the amount of fiber
Symbols used in the figure: ○ Example 1
◻ Example 2  △ Example 3
▽ Example 4a  ◇ Example 4b
⬭ Example 5b  ⊙ Example 7a
◐ Example 7b  ▼ 0-test (no ASA)
◧ Example 6

ALKENYL SUBSTITUTED CYCLIC CARBOXYL ACID ANHYDRIDES AND THEIR APPLICATION IN HYDROPHOBIC PAPER SIZING

This application is a 371 PCT/FI95/00541 filed on Oct. 04, 1995.

The present invention relates to new alkene-substituted cyclic carboxylic acid anhydrides. Of these, in particular alkene-substituted succinic acid anhydrides, i.e. so-called ASA sizing agents, are used, for example; in the hydrophobic sizing of paper. The invention also relates to a process for preparing these anhydrides. Furthermore, the invention relates to a method of hydrophobic paper sizing within the neutral or the alkaline pH range by using ASA sizing agents prepared by the process according to the invention.

Paper or cardboard material is usually treated in connection with manufacture or finishing with so-called sizing agents in order to produce a hydrophobic paper material. The purpose of this procedure is to reduce the penetration and adsorption of water and other liquids, such as ink, into the paper. Only sized paper is suitable for printing and writing purposes.

Usually the hydrophobic sizing of paper or cardboard material is carried out by using substituted cyclic carboxylic acid anhydrides, the most commonly used among them being substituted succinic acid anhydrides. The substituents may be alkyl, alkene, aralkyl or aralkene groups, as disclosed in, for example; U.S. Pat. No. 3 102 064. Alkene substituents are the most commonly used.

Alkene-substituted succinic acid anhydrides are prepared by a simple method by allowing an alkene compound to react with maleic anhydride at a temperature of 150–250° C.

U.S. Pat. No. 3 821 069 discloses for the sizing of paper an alkene-substituted succinic acid anhydride the alkene substituent of which comprises an internal olefin preferably having 14–22 carbon atoms. The double bond of the olefin is at least in position 6 in the carbon chain.

GP patent publication 2 015 612 discloses for the neutral sizing of paper the use of an aqueous emulsion of a butene oligomer substituted succinic acid anhydride. The oligomer comprises 16–40 carbon atoms, and it is obtained through the oligomerization of 1-butene, 2-butene or isobutylene, the last-mentioned being the most preferable. The aqueous emulsion is prepared by using preferably cationic starch. For improving sizing efficacy, the method according to the publication uses a cationic retention agent, for example, a commercially available water-soluble cross-bridged polyamidoamine.

U.S. Pat. No. 4 576 680 discloses for use for the sizing of paper the reaction product of maleic anhydride and a branched internal 14–36 carbon atom olefin oligomer. The oligomer is formed from one or several olefins containing 6–18 carbon atoms. The double bond in the chain is at least in position 3. For the preparation of the sizing agent emulsion there are additionally needed a dispersing agent, such as cationic starch, and an emulsifier, such as certain fatty acids, ethers, phenols, esters, and their acetylated products.

JP patent publication 61 172 866 discloses for the sizing of paper an alkene-substituted succinic acid anhydride in which the alkene substituent is a 12–22 carbon atom straight-chain 1-olefin obtained by oligomerizing ethylene, by dehydrochlorinating chlorinated paraffin, or by decomposing wax or the like.

In the process according to EP patent publication 522564, the alkene substituent used in the substituted succinic acid anhydride intended for paper sizing consists of straight-chain internal olefins containing 16–20 carbon atoms.

In JP patent publication 57 154 496, the alkene substituent in the succinic acid anhydride is also made up of linear, internal olefins. However, if internal olefins are used for the preparation of ASA sizing agents, sizing agents are obtained which have a high reactivity with respect to paper fiber, but on the other hand they also have a high hydrolysis rate in water, and thus it is difficult to obtain an emulsion sufficiently stable for paper making. The poor stability of the emulsion thus results in that the useful life of the emulsion is short and that it is difficult to obtain on the paper surface a uniform-quality ASA neutral sizing agent.

It should be noted additionally that, according to said patent publications GB 2 015 612 and U.S. Pat. No. 4 576 680, an oligomerization product prepared from butene olefins, in particular from t-butene, is not as such suitable for use as an initial material for an ASA neutral sizing agent; other additives are required in addition to the conventional cationic starch in order to obtain a high sizing efficacy.

To eliminate the disadvantages stated above, an object of the present invention is to prepare new alkene-substituted cyclic carboxylic acid anhydrides.

It is also an object of the invention to present new processes for the preparation of alkene-substituted cyclic carboxylic acid anhydrides.

It is a particular object of the invention to produce new alkene-substituted succinic acid anhydrides by preparation processes according to the invention.

Furthermore, it is an object of the invention to prepare, for purposes of hydrophobic sizing of paper, alkene succinic acid type sizing agents, so-called ASA sizing agents, which can be used within the neutral or the alkaline pH range and which make it possible, for example, to use calcium carbonate type preferred fillers in the paper.

It is a further object of the invention to produce such ASA-type neutral sizing agents that the hydrolysis rate of emulsions made therefrom will be optimal for paper making and that, when applied to paper surface, the said emulsions will be of uniform quality.

It is an additional object of the invention to find a method for efficient and optimal hydrophobic sizing of paper.

It is one further object of the invention to produce alkene-substituted succinic acid anhydrides which are used as various additives in, for example, fire-retarding plastics, the hardening of epoxy resins, and also in the form of salts in, for example, the thermal stabilization of PVC and in the form of imides as fuel and lubricant dispersing agents.

It has now been observed, surprisingly, that the new alkene-substituted cyclic carboxylic acid anhydrides according to the present invention can be prepared by using olefinic initial materials according to the invention, prepared by processes according to the invention. In particular, the said properties maximally optimal for, for example, paper sizing are accomplished by using the new alkene-substituted succinic acid anhydrides according to the invention. The alkene-substituted cyclic carboxylic acid anhydrides according to the invention are characterized in what is stated in the characterizing clause of claim 1.

The alkene substituents of cyclic alkene-substituted carboxylic acid anhydrides disclosed in claim 1, and further cyclic acid anhydrides prepared therefrom, can be prepared by methods which are characterized in what is stated in the characterizing clause of any of claims 6–16.

The use of cyclic alkene-substituted carboxylic acid anhydrides, in particular alkene-substituted succinic acid anhydrides, as so-called ASA sizing agents in the hydrophobic sizing of paper is disclosed in claim 17, and a method for the hydrophobic sizing of paper is disclosed in claim 19.

Alkene-substituted cyclic carboxylic acid anhydrides are prepared by allowing an olefin component to react with a corresponding cyclic anhydride having a double bond, in particular with maleic acid anhydride.

In the preparation of an alkene-substituted succinic acid anhydride, the olefin component is allowed to react with maleic acid anhydride at approx. 160–250° C. for approx. 2–6 hours. The ratio of olefin to maleic acid anhydride is 1–4:1. Any unreacted olefin and maleic acid anhydride is removed by distillation. The olefin and the maleic acid anhydride may thus be reacted by using merely heat. For the purity and total yield of the final product, however, it is preferable in the process according to the invention to use additives, i.e. inhibitors, which inhibit the formation of byproducts. Such inhibitors include hydroquinones, sterically hindered phenols, boric acid, etc. It is especially preferable to use as an additive a blend of boric acid and hindered phenol, such as di-tert-butyl-hydroxytoluene (BHT), wherein the ratio of acid to phenol is preferably 1:1. The reaction mixture may contain the blend in an amount of approx. 0.1–2.0% by weight, calculated from the total mass of the olefin blend and the maleic acid anhydride.

The selection of the alkene-substituent for the alkene-substituted cyclic carboxylic acid anhydrides, such as succinic acid anhydrides, plays a significant role in the useful properties of the product, such as its usability in the hydrophobic sizing of paper.

The olefin component which is used in the preparation of the alkene-substituted cyclic carboxylic acid anhydrides, in particular alkene-substituted succinic acid anhydrides, according to the invention, and which is prepared by the method described in greater detail below, comprises a blend of olefins having 13–25 carbon atoms. The number-average carbon number of the blend is preferably 14–17, most preferably it is 15–16. The best results in the ASA sizing of paper are obtained, i.e. the permeability of the paper to water is significantly reduced, when the number-average carbon number is within the preferred range of 14–17. The olefin blend contains both alpha-olefins and internal clefins, the carbon number being even or odd. Both the $\alpha$-olefins and the internal olefins may be either linear, i.e. straight-chain, and/or branched olefins. The ratio of $\alpha$-olefins to internal olefins in the olefin blend may vary within a wide range, which means an alpha-olefin amount of approx. 5–95%, the amount of internal olefins being 95–5%. Most preferably the olefin blend contains alpha-olefins in an amount of 50–95%, and most preferably 70–90%, the amount of internal olefins being respectively 5–50%, most preferably 10–30%.

It has now been observed, surprisingly, that the olefin blend according to the invention, used as an initial material for substituted succinic acid anhydride, can be prepared by oligomerizing a preferred blend of 1-butene and 2-butene, a so-called Raffinate II stream, from which the 4-carbon isobutene olefin has been removed by reacting it with methanol. The oligomerizing of the n-butenes present in Raffinate II and suitable for further use can be carried out by using a batch, semi-batch or continuous-working process. The catalysts used are either homogenous or heterogenous catalysts. Especially suitable homogenous catalyst systems include $BF_3$ alcohol complexes or carboxylic acid complexes or various Al catalysts, such as $AlCl_3$—HCl catalyst, $AlCl_2CH_2CH_3$ catalyst or $AlCl_3$ aromate catalyst. The heterogenous oligomerization catalyst used, for its part, may be a synthetic aluminum silicate. In particular the structure of the olefin fraction of poly-n-butenes, and thereby the properties of the product, can be affected by the selection of the catalyst. The desired olefin fraction, containing 13–25 carbon atoms, which in accordance with the invention contains both internal and alpha-olefins, can be separated from the product blend by distillation. The obtained olefin fraction may also contain lesser amounts of alkanes as inert solvent components.

An olefinic initial material, suitable considering the hydrophobic sizing of paper, for the succinic acid anhydride can also be obtained by dehydrogenating one or several branched alcohols having 6–10 carbon atoms to a corresponding olefin blend and by dimerizing the said blend by using, for example, the above-mentioned acid catalysts. Preferably the dimerization catalyst is a $BF_3$ alcohol complex. The result obtained will be an olefin blend which contains, in accordance with the invention, both alpha olefins and internal olefins having 13–25 carbon atoms. Especially suitable branched alcohols to be dehydrogenated include commercially available 2-propylheptanol and 2-ethylhexanol.

The alkene-substituted cyclic carboxylic acid anhydride can also be prepared from an olefin prepared, surprisingly and advantageously, by pyrolyzing at a high temperature, i.e. at approx. 300–500° C., a high molecular weight polyethylene waste obtained from recycling. The olefin blend suitable for use as the initial material for ASA is obtained by separating from the pyrolyzate by distillation an olefin blend made up of olefin chains containing 13–25 carbon atoms. The said olefin blend contains both alpha and internal olefins, the former in an amount of approx. 50–95%, preferably approx. 70–90%, and the latter in an amount of approx. 50–5%, preferably approx. 30–10%. The pyrolysis fractions additionally contain alkanes as solvent components. The ratio of alkanes to olefins is within the range 20:80–80:20, preferably within the range 30:70–70:30, and most preferably within the range 40:60–60:40. The properties of ASA sizing agents prepared from olefins prepared by this procedure are as good as the properties of ASA sizing agents prepared from pure initial materials. Furthermore, the polyethylene waste can be exploited efficiently, which of course reduces the costs of waste treatment.

The olefin blend component according to the invention, necessary for the preparation of an ASA sizing agent, can, of course, also be prepared by mixing commercially available alpha-olefins and internal olefins having 13–25 carbon atoms, these olefins forming the desired olefin blend in which the proportion of $\alpha$-olefin is 5–95%, preferably 50–95%, and most preferably 70–90% and the number-average carbon number is preferably 14–17, most preferably 15–16.

By the methods described above, an olefin component suitable for use as an initial material for an alkene-substituted carboxylic acid anhydride, in particular and alkene-substituted succinic acid anhydride usable for ASA neutral sizing, is obtained advantageously from, for example, byproducts or wastes of other production. The olefin component (olefin blend) obtained by the methods described above has a carbon number, blend proportions and olefin chain structure highly suitable for producing highly usable properties for the hydrophobic sizing of paper within the neutral and the alkaline pH range. The ASA sizing agent according to the invention, for example, enables preferred fillers of the calcium carbonate type to be used in the paper.

The ASA sizing agents described above are used in paper-making in the form of dilute emulsions, which are prepared by using a colloidal dispersing agent, such as cationic starch, cationic polyacrylamine, poly(di-alkyl-dimethylammonium chloride), synthetic polyamine or polyethylene imine. It is especially suitable to use cationic starch in ASA sizing emulsions according to the invention. The ratio of starch to ASA sizing agent in a 0.1–10 wt. % aqueous solution is preferably within the range 0.5–10:1, preferably within the range 1–5:1, within the acid pH range (pH≦6). Emulsions thus prepared are stable at room temperature for up to 7 days. When ASA sizing agents according to the present invention are used in the ASA sizing of paper or cardboard material, the suitable amount of ASA sizing agent in the fiber material for obtaining an optimal sizing efficacy is within the range 0.1–1.5% by weight ASA of the amount of fiber, preferably 0.1–1% by weight ASA of the amount of fiber, and most preferably the amount of ASA is within the range 0.3–0.5% by weight.

The invention is described in greater detail in the following examples and figures. However, they are not to be taken as limiting the invention; they are intended only to illustrate the invention.

FIG. 1. Water permeability of paper when ASA sizing agents according to the invention and prior known ASA sizing agents are used.

FIG. 1 shows the water permeability of ASA-sized experimental paper sheets, measured by a paper sizing test according to the COBB 60 index. According to the test, the amount of water adsorbed to the paper within 60 seconds at pH 7 was measured. Tests were performed using ASA concentrations of 0.1, 0.3, 0.5 and 1% by weight ASA of the amount of fiber. The reference test (so-called zero test) was a completely untreated paper.

The symbols in FIG. 1 refer to the examples as follows:

| Example | Symbol |
|---|---|
| 1 | white circle |
| 2 | white square |
| 3 | white triangle |
| 4a | inverted white triangle |
| 4b | white diamond |
| 5b | hexagon |
| 6 | half-shaded square |
| 7a | white circle with a cross |
| 7b | half-shaded circle |

Zero test:inverted triangle with a cross The zero test gave as a result 420 g/m² as the amount of adsorbed water.

EXAMPLE 1,

Reference Example

Effect of inhibitor on the reaction between olefin and acid anhydride.

A Parr high-pressure reactor was charged with 1-hexadecene, which had been prepared by oligomerizing ethylene, and with maleic acid anhydride (MHA), at the molar ratio 1.2:1, as well as with an inhibitor, if any, as follows:

a) no inhibitor;
b) inhibitor 0.5% by weight boric acid, $H_3BO_3$;
c) inhibitor 0.5% by weight di-tert-butylhydroxytoluene (BHT);
d) inhibitor a mixture of $H_3BO_3$ 0.2% by weight and BHT 0.2% by weight.

The amount of inhibitor is calculated from the total combined mass of olefin and MHA.

The reactor was closed and rinsed with gaseous nitrogen, whereafter it was heated to 220° C. and was kept at this temperature for 5 h, the mixing, at 600 rpm, being on throughout the reaction. The product was analyzed by gas chromatography. The results are shown in Table 1.

TABLE 1

Effect of inhibitor on the yield of ASA

| Reaction | Inhibitor | ASA yield, wt. % |
|---|---|---|
| a | — | 62 |
| b | 0.5 wt. % $H_3BO_3$ | 56 |
| c | 0.5 wt. % BET | 51 |
| d | 0.2 wt. % $H_3BO_3$ 0.2 wt. % BHT | 79 |

The product was purified by removing by vacuum distillation any unreacted initial materials, 1-hexadecene and MHA.

From the conventional ASA product thus prepared, an ASA emulsion was prepared as an aqueous solution by using a dispersing agent, at a temperature of 20° C. and a pH of 2.5. The molar ratio of dispersing agent to ASA was 2:1. The dispersing agent used was cationic starch or a synthetic polyamine-poly-DADMAC dispersing agent commonly used in the art.

The stability of he emulsion and the changes occurring therein were studied by determining the homogeneity (A) of the emulsion, the creaming (B) and coalescence (C) appearing in the emulsion, and the decomposition (D) of the emulsion, at different concentrations of the said dispersing agent at 20° C. The pH of the newly prepared emulsions was 2.5. The results are shown in Tables 2a and 2b. The tables indicate in hours the time which elapsed from the completion of the emulsion to the appearance of the phenomenon concerned. In Table 2a the dispersing agent is starch and in Table 2b it is poly-DADMAC.

TABLE 2a

Time which elapsed to the changes occurring in the emulsion, as a function of the starch concentration

| disp/wt. % | 0 | 0.05 | 0.1 | 0.2 | 0.5 | 1 | 2 | 3 | 4 |
|---|---|---|---|---|---|---|---|---|---|
| A | 0 | 0 | 0 | 0 | 0 | 0 | 0 | 0 | 0 |
| B | 0.2 | 0.2 | 0.5 | 1 | 1 | 3 | * | * | * |
| C | 4 | 5 | * | * | * | * | * | * | * |
| D | 23 | 96 | * | * | * | * | * | * | * |

* = more than 7 days

TABLE 2b

Time which elapsed to the changes occurring in the emulsion, as a function of the poly-DADMAC concentration

| disp/wt. % | 0 | 0.05 | 0.1 | 0.2 | 0.5 | 1 | 2 | 3 | 4 |
|---|---|---|---|---|---|---|---|---|---|
| A | 0 | 0 | 0 | 0 | 0 | 0 | 0 | 0 | 0 |
| B | 0.01 | 1 | 0.7 | 0.2 | 0.5 | 2 | 0.2 | 1.5 | 3.3 |
| C | 1.2 | 9 | 1 | 1 | 0.8 | 3 | 4 | 11 | 24 |
| D | 9 | 24 | 24 | 24 | * | * | * | * | * |

* = more than 7 days

The neutral sizing test method used was the paper sizing test according to the COBB 60 index. The result of the test was 39.10 g/m² when the ASA concentration was 1% by weight. This is shown in FIG. 1, in which the result according to Example 1 is indicated by a white circle.

EXAMPLE 2

A commercial blend of hexadecene and octadecene, which contained 2.3% tetradecene, 74.2% hexadecene and 23.5% octadecene, and in which the proportion of linear olefins was 90–95% and the proportion of internal olefins was 5–10% and the proportion of branched olefins 5–10%, was allowed to react with MHA in the presence of an inhibitor (0.2% by weight $H_3BO_3$ and 0.2% by weight BHT). The reaction product was emulsified by using cationic starch as the dispersing agent. Water permeability was measured at ASA concentrations of 0.3, 0.5 and 1% by weight ASA of the amount of fiber. The water permeability results obtained by the COBB 60 test were 16.5, 18.6 and 13.5 $g/m^2$, the respective ASA concentrations being 0.3, 0.5 and 1.0% by weight. The water permeability of paper thus prepared, treated with the ASA sizing emulsion, for example at a concentration of 1% by weight ASA of the amount of fiber, was thus approximately 20 times lower than that of untreated paper, which is shown in FIG. 1 (the results are indicated by an inverted triangle with a cross).

EXAMPLE 3

2-Propyl-heptanol was dehydrogenated catalytically by using $Al_2O_3$ catalyst at 300–500° C. The result obtained was an olefin blend which contained 60% 2-propyl-1-heptene and 40% internal olefins having the same basic carbon structure. This decene blend was oligomerized by using as the catalyst a $BF_3$ butanol complex at a temperature of 10–40° C. and a $BF_3$ pressure of 0.5–3 bar, for 0.5–4 hours. The dimer fraction was separated by vacuum distillation from the produced oligomer blend.

The dimerization product was allowed to react with MHA by charging a Parr high-pressure reactor with the dimerization product (150.2 g, 0.67 mol), MHA (44.0 g, 0.45 mol) as well as 0.4 g of $H_3BO_3$ and 0.4 g BHT. The reactor was closed and rinsed with gaseous nitrogen, whereafter it was heated to 220° C. and was kept at this temperature for 5 h, the mixing being on throughout the reaction. Any unreacted initial materials were removed by vacuum distillation. The yield of the obtained alkene-substituted succinic acid anhydride was 67%.

ASA prepared in accordance with the above was emulsified as above. Neutral sizing of paper was carried out using the obtained emulsion. The water permeability of the paper treated with the ASA sizing agent prepared by this method according to the invention, containing 0.3% by weight ASA of the amount of fiber, was 85.6 $g/m^2$, which is indicated by a white triangle in FIG. 1.

EXAMPLE 4

A so-called Raffinate II stream, which contained 14% 1-butene, 28% 2-butene, 7% iso-butene and 51% butane and other impurities, was oligomerized by using as the catalyst a synthetic silica-alumina and a continuous-working reactor. The carbon number of the olefin fraction boiling within the temperature range 250–450° C. at normal pressure, and containing both branched internal and alpha-olefins, was within the range 14–25.

a) From this produced oligomer blend, a fraction having at normal pressure a boiling point range of 280–300° C., which by its number-average carbon number corresponds to $C_{16}$ hydrocarbons, was separated by vacuum distillation. 146.3 g of the blend obtained from this vacuum distillation was reacted with 53.6 g of MHA at 200° C. for 23 hours. 0.4% of BHT and 0.4% of $H_3BO_3$, calculated from the total mass of MHA and olefin, were used in the reaction. The yield of ASA obtained was 61.6 g.

b) From the produced oligomer blend, a fraction having at normal pressure a boiling point range of 270–340° C., which by its number-average carbon number corresponds to $C_{18}$ hydrocarbons, was separated by vacuum distillation. 75.8 g of the blend obtained from this vacuum distillation was reacted with 23.8 g of MHA at 220° C. for 4 hours. 0.2% by weight BHT and 0.2% by weight $H_3BO_3$, calculated from the total mass of MHA and olefin, were used in the reaction. The yield of ASA obtained was 57.6%.

c) From the produced oligomer blend, a fraction having at normal pressure a boiling point of 270° C., which by its number-average carbon number corresponds to $C_{20}$ hydrocarbons, was separated by vacuum distillation. 76.7 g of the blend obtained from this vacuum distillation was reacted with 22.9 g of MHA at 220° C. for 4 hours. 0.2% by weight BHT and 0.2% by weight $H_3BO_3$, calculated from the total mass of MHA and olefin, were used in the reaction. The yield of ASA obtained was 56.8%.

The products from a) and b) were emulsified, and their neutral sizing efficacies were tested as above. The water permeability values determined using the COBB 60 test were in case a) 22.5, 16.4 and 17.6 $g/m^2$ when the ASA concentrations were respectively 0.3, 0.5 and 1.0% by weight/fiber, which is indicated in FIG. 1 by a white diamond.

EXAMPLE 5

The Raffinate II stream described in Example 4 was oligomerized by using a $BF_3$ cocatalyst complex at a temperature of 20–50° C. and a $BF_3$ pressure of 1–10 bar for 0.5–6 hours. Fractions having primary carbon numbers of a) $C_{12}$, b) $C_{16}$ and c) $C_{20}$ were separated by vacuum distillation from the produced oligomer blend. Table 3 shows the concentrations of the oligomers present in the various fractions.

TABLE 3

| Concentrations of the oligomers present in the various fractions | | | | |
|---|---|---|---|---|
| | $C_{12}$/wt. % | $C_{16}$/wt. % | $C_{20}$/wt. % | $C_{24+}$/wt. % |
| fraction a) | 85.0 | 15.0 | — | — |
| fraction b) | 0.5 | 94.5 | 5.0 | — |
| fraction c) | — | 6.1 | 83.0 | 10.9 |

Each fraction contained approx. 80% branched both internal and alpha-olefins and approx. 20% alkanes. Each olefin fraction was reacted with MHA at the molar ratio 1.2:1 at 220° C. for 4–5 hours. 0.2% by weight BHT and 0.2% by weight $H_3BO_3$, calculated from the total mass of MHA and olefin, were used in the reactions. The yields of the ASA product were:

| | |
|---|---|
| fraction a) $C_{12}$ | 55.7% |
| fraction b) $C_{16}$ | 57.7% |
| fraction c) $C_{20}$ | 52.3% |

The product which had been formed in a reaction between fraction b) ($C_{16}$) and MHA and from which any unreacted initial materials had been removed by distillation was emulsified by using cationic starch and was tested as above at ASA concentrations of 0.3, 0.5 and 1.0 mg of ASA/g of fiber. The results were respectively 21.0, 16.3 and 14.1 $g/m^2$, and they are indicated in FIG. 1 by a hexagon.

EXAMPLE 6

The olefin component required for the preparation of ASA was prepared by pyrolyzing a polyethylene waste at a temperature of 350–600° C. and a pressure of 1–25 bar. A fraction having carbon chains containing 13–16 carbon atoms and a number-average molar mass of approx. 200 g/mol was separated by vacuum distillation from the hydrocarbon blend formed. In this fraction the alkene/alkane ratio was $^{40}\!/_{60}$. This hydrocarbon fraction was reacted with MHA at 220° C. for approx. 5 hours. The ASA yield obtained was 59.0%. 0.2% by weight BHT and 0.2% $H_3BO_3$, calculated from the total mass of olefin and MHA, were used in the reactions.

The product was emulsified and tested as above at an ASA concentration of 1.0% by weight/fiber, the water permeability obtained being 62.5 g/m². The result is indicated in FIG. 1 by a half-shaded square.

EXAMPLE 7

To a fraction of olefin chains having 16–18 carbon atoms according to Example 2 (55.8 g)an olefin fraction having a number-average carbon number of 18 according to Example 4 b) was added so that the ratio of the former to the latter was a) 80:20 and b) 50:50. The obtained blend was allowed to react with MHA at 220° C. for 4.5 hours in the presence of an inhibitor (0.2% by weight BHT and 0.2% by weight $H_3BO_3$).

The product was emulsified by using cationic starch and was tested as above. The results are shown in the following table.

| Example | ASA concentration wt. % | COBB 60 test g/m² |
|---|---|---|
| 7 a) | 0.3 | 16.0 |
| 7 a) | 0.5 | 16.4 |
| 7 a) | 1.0 | 11.8 |
| 7 b) | 0.3 | 49.3 |
| 7 b) | 0.5 | 19.7 |
| 7 b) | 1.0 | 15.5 |

These results are indicated in FIG. 1 in case a(a) by a white circle with a cross and in case (b) with a half-shaded circle.

We claim:

1. An alkene-substituted cyclic carboxylic acid anhydride obtained by the reaction comprising:
   reacting (A) a cyclic carboxylic acid anhydride and (B) an olefin blend, wherein said olefin blend comprises 5–95% by weight of the total weight of the olefin blend linear and branched internal olefins having 13–25 carbon atoms and 95–5% by weight of the total weight of the olefin blend of linear and/or branched alpha-olefins having 13–25 carbon atoms obtained by oligomerization of a blend consisting essentially of 1-butene and 2-butene.

2. The alkene-substituted cyclic carboxylic acid anhydride according to claim 1, wherein the cyclic carboxylic acid anhydride is a succinic acid anhydride.

3. The alkene-substituted cyclic carboxylic acid anhydride according to claim 1 or 2, wherein the number-average carbon number of the internal olefins and alpha-olefins is within the range of 14–17.

4. The alkene-substituted cyclic carboxylic acid anhydride according to claim 3, wherein said number-average carbon number is within the range of 15 to 16.

5. The alkene-substituted cyclic carboxylic acid anhydride according to claim 1, wherein the olefin blend contains alpha-olefins in an amount of 5–95% and internal olefins in an amount of 95–5%.

6. The alkene-substituted cyclic carboxylic acid anhydride according to claim 5, which contains alpha-olefins in an amount of 50–95% and internal olefins in an amount of 5–50%.

7. The alkene-substituted cyclic carboxylic acid anhydride according to claim 5, which contains alpha-olefins in an amount of 70–90% and internal olefins in an amount of 10–30%.

8. The alkene-substituted cyclic carboxylic acid anhydride according to claim 1, wherein said olefin blend further comprises alkanes, the percentage ratio of olefins to alkanes being 80:20–20:80.

9. The alkene-substituted cyclic carboxylic acid anhydride according to claim 8, wherein said percentage ratio of olefins to alkanes is 70:30–30:70.

10. The alkene-substituted cyclic carboxylic acid anhydride according to claim 8, wherein said percentage ratio of olefins to alkanes is 60:40–40:60.

11. A process for the preparation of an alkene-substituted cyclic carboxylic acid anhydride which comprises allowing an olefin to react under heat with a corresponding cyclic anhydride having a double bond, wherein the olefin component is obtained by oligomerizing, by using a homogeneous or heterogeneous catalyst, a blend consisting essentially of 1-butene and 2-butene.

12. The process according to claim 11, wherein said anhydride is maleic acid anhydride.

13. The process according to claim 11, wherein the homogenous catalyst used consists of complexes of $BF_3$, alcohol or carboxylic acid, or of various Al catalysts such as $AlCl_3$—HCl catalysts, $AlCl_2CH_2CH_3$ catalysts or $AlCl_3$ aromate catalysts, and the heterogenous catalyst used is a synthetic aluminum silicate.

14. The process according to claim 13, wherein said catalyst is an acid catalyst.

15. The process according to claim 14, wherein said acid catalyst is a $BF_3$ alcohol complex.

16. The process according to claim 11 wherein an inhibitor is used for inhibiting the formation of byproducts.

17. The process according to claim 16, wherein said inhibitor is boric acid, tert-butylhydroxytoluene or mixtures thereof.

18. The process according to claim 16, wherein the inhibitor used is a 1:1 mixture of boric acid and di-tert-butylhydroxytoluene, in which each is present in an amount of 0.05–1.0% by weight, of the total mass of the olefin and the acid anhydride.

19. A method of using an alkene-substituted succinic acid anhydride according to claim 3 as an aqueous emulsion in the hydrophobic sizing of paper or cardboard fiber material.

20. A method according to claim 19, wherein said use is at a neutral or alkaline pH.

21. A process for the hydrophobic sizing of paper or cardboard material with an alkene-substituted succinic acid anhydride sizing agent wherein the paper or cardboard fiber material is treated, in connection with the manufacture or finishing, with an ASA sizing agent which comprises a reaction product of succinic acid anhydride and the olefin blend defined in claim 1, from which product an aqueous emulsion has been prepared by using a dispersing agent.

22. The process according to claim 21, wherein a dispersing agent is used selected from the group consisting of cationic starch, cationic polyacrylamine, poly(di-alkyl-dimethylammonium chloride) or polyethylene imine.

23. The process according to claim 22, wherein the ratio of the dispersing agent to the ASA product in a 0.1–10 wt.% aqueous solution is within the range 0.5–10:1.

24. The process according to claim 21, wherein the ASA sizing agent is used at a concentration of 0.01–1% by weight of the amount of fiber.

25. The alkene-substituted cyclic carboxylic acid anhydride according to claim 1, wherein said olefin blend further comprises one or several other olefins.

26. The alkene-substituted cyclic carboxylic acid anhydride according to claim 1, wherein said cyclic carboxylic acid anhydride and said olefin blend are further reacted with an inhibitor.

* * * * *